(12) United States Patent
Kuo et al.

(10) Patent No.: US 7,725,152 B2
(45) Date of Patent: *May 25, 2010

(54) EXTENDED OPTICAL RANGE SYSTEM FOR MONITORING MOTION OF A MEMBER

(75) Inventors: Chia Chyuan Kuo, Wilmington, DE (US); George W. Coulston, Pittsburgh, PA (US)

(73) Assignee: Textronics, Inc., Wilmington, DE (US)

( * ) Notice: Subject to any disclaimer, the term of this patent is extended or adjusted under 35 U.S.C. 154(b) by 568 days.

This patent is subject to a terminal disclaimer.

(21) Appl. No.: 10/937,120

(22) Filed: Sep. 9, 2004

(65) Prior Publication Data
US 2005/0118914 A1 Jun. 2, 2005

Related U.S. Application Data

(60) Provisional application No. 60/502,760, filed on Sep. 12, 2003, provisional application No. 60/502,751, filed on Sep. 12, 2003, provisional application No. 60/502,750, filed on Sep. 12, 2003, provisional application No. 60/526,187, filed on Dec. 2, 2003, provisional application No. 60/526,429, filed on Dec. 2, 2003, provisional application No. 60/526,188, filed on Dec. 2, 2003.

(51) Int. Cl.
*A61B 5/02* (2006.01)

(52) U.S. Cl. .................. 600/407; 442/184; 442/301; 442/306; 442/182; 2/1; 600/473; 600/476; 600/479; 600/534; 600/595; 250/221; 250/559.4; 250/559.01; 250/559.12; 250/559.16; 250/222.1; 356/238.1; 356/238.2; 356/238.3; 356/239.1; 356/239.2; 356/239.3; 356/429; 356/430; 356/431

(58) Field of Classification Search .............. 442/182, 442/184, 306, 301; 600/485, 499, 490, 407, 600/473, 476, 479, 534, 595; 2/1; 250/221, 250/559.4, 559.01, 559.12, 559.16, 222.1, 250/559.44; 356/238.1–239.3, 429–431
See application file for complete search history.

(56) References Cited

U.S. PATENT DOCUMENTS 3,517,999 A * 6/1970 Weaver .................. 356/32

(Continued)

FOREIGN PATENT DOCUMENTS

WO WO-97/14357 4/1997

OTHER PUBLICATIONS

Salutron Technology Evaluation Data Summary from www.Salutron.com.

*Primary Examiner*—Elizabeth M Cole
(74) *Attorney, Agent, or Firm*—Connolly Bove Lodge & Hutz LLP

(57) ABSTRACT

A garment and system includes a monitoring fabric comprising a first plurality of reflective yarns knitted or woven with a second plurality of stretchable yarns. The fabric exhibits both a light transmission property and a light reflection property. The amount of light transmitted through the fabric relative to the amount of light reflected by the fabric changes when the fabric stretches in response to motion, such as the motion induced by physiological activity (e.g., heart rate). The system includes at least one source of radiation having wavelength(s) in the range of 400 to 2200 nanometers and at least one detector responsive to such incident radiation. The source and detector are associated with the fabric such that the reception of incident radiation by the detector is directly affected by a change in the amount of light transmitted through the fabric relative to the amount of light reflected by the fabric when the fabric stretches. A signal processor converts a signal from the detector into a signal representative of at least one predetermined physiological parameter of a wearer of the garment.

12 Claims, 10 Drawing Sheets

U.S. PATENT DOCUMENTS

| | | |
|---|---|---|
| 4,909,260 A | 3/1990 | Salem et al. |
| 4,920,969 A * | 5/1990 | Suzuki et al. ............... 600/436 |
| 5,577,510 A | 11/1996 | Okuda et al. |
| 5,703,688 A * | 12/1997 | Bell ........................... 356/430 |
| 5,820,567 A | 10/1998 | Mackie |
| 5,840,037 A | 11/1998 | Tochikubo et al. |
| 6,168,567 B1 | 1/2001 | Pickering et al. |
| 6,224,558 B1 | 5/2001 | Clemmons |
| 6,315,009 B1 * | 11/2001 | Jayaraman et al. ...... 139/387 R |
| 6,322,516 B1 | 11/2001 | Masuda et al. |
| 6,341,504 B1 | 1/2002 | Istook |
| 6,360,615 B1 | 3/2002 | Smela |
| 6,842,722 B2 | 1/2005 | David et al. |
| 2003/0095263 A1 * | 5/2003 | Varshneya et al. .......... 356/477 |
| 2005/0106977 A1 | 5/2005 | Coulston |
| 2005/0277837 A1 | 12/2005 | Coulston et al. |
| 2007/0042179 A1 | 2/2007 | Karayianni et al. |

\* cited by examiner

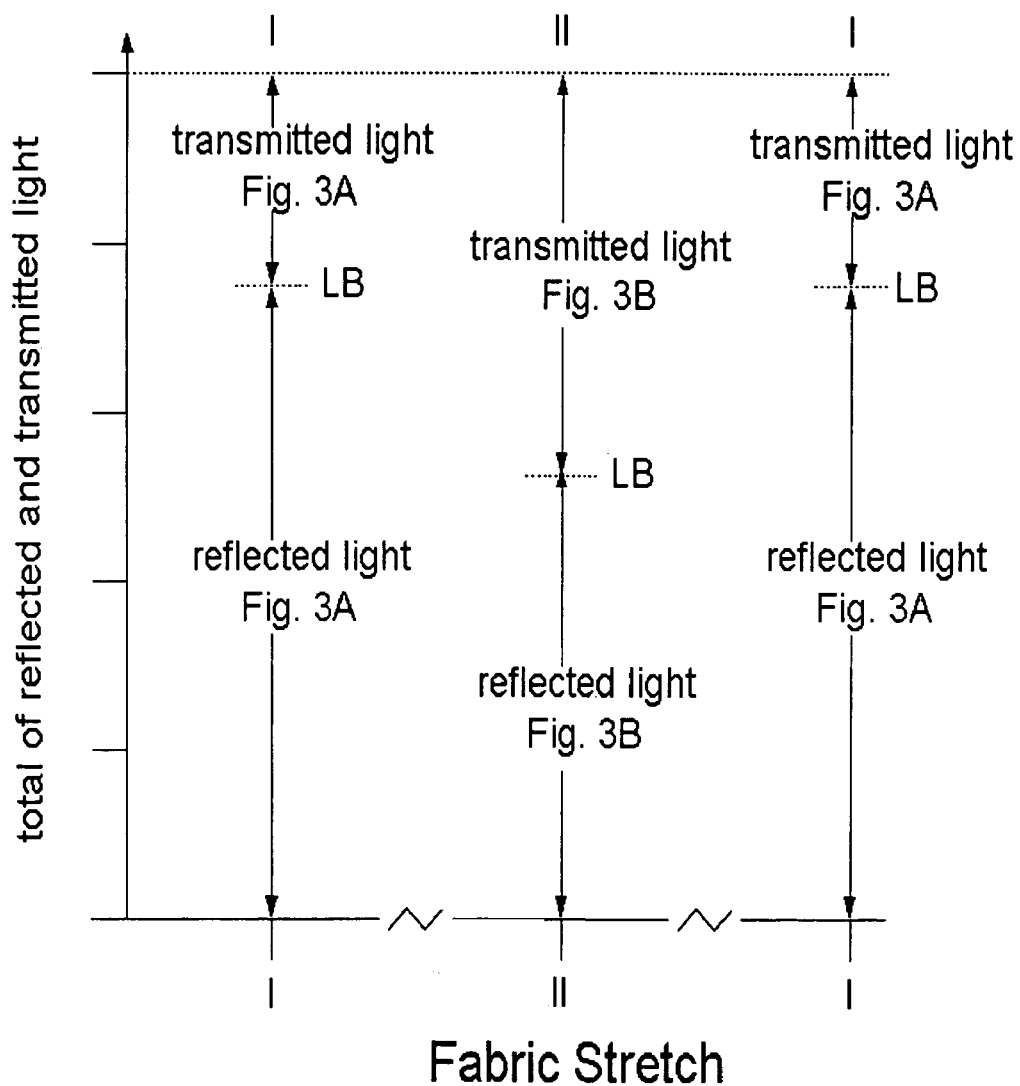

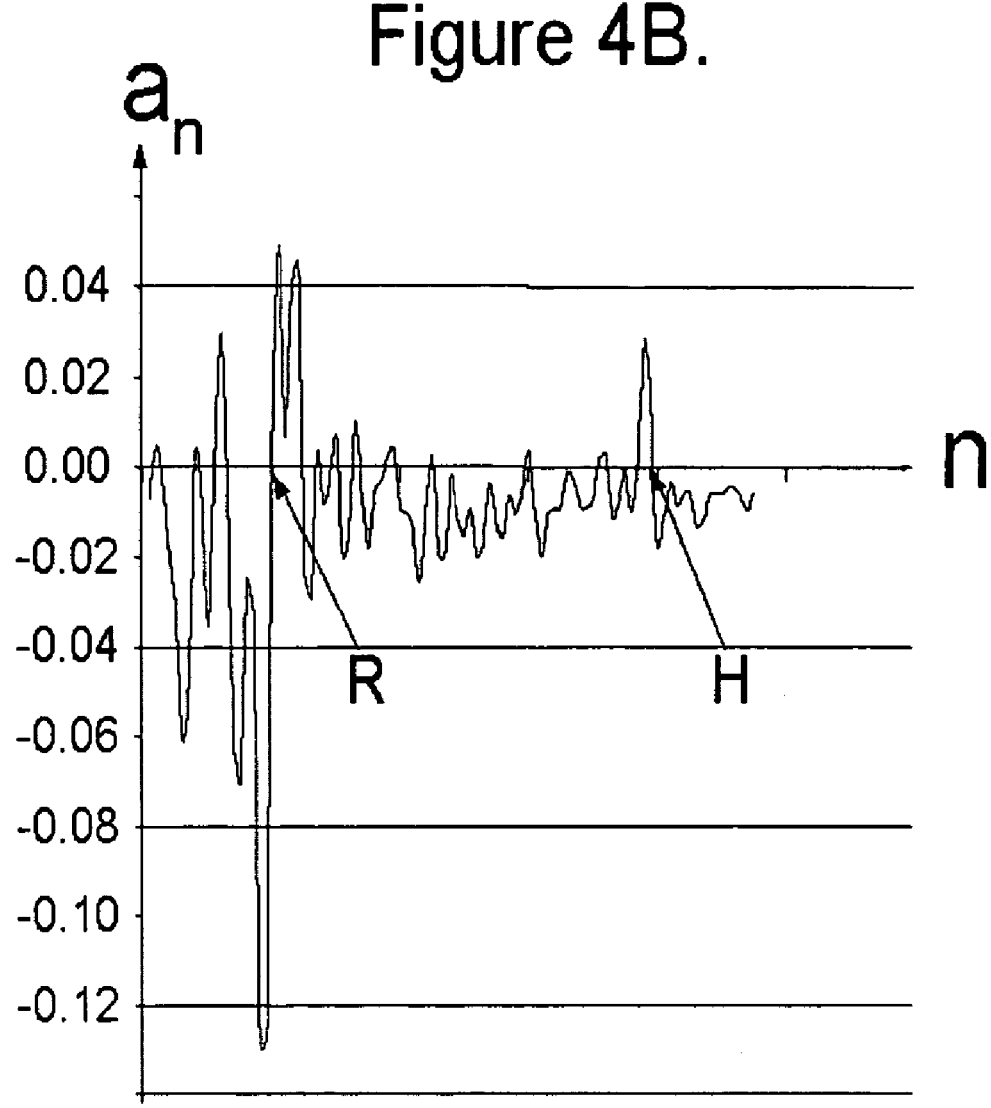

EXTENDED OPTICAL RANGE SYSTEM FOR MONITORING MOTION OF A MEMBER

CROSS-REFERENCE TO RELATED APPLICATIONS

Subject matter disclosed herein is related to the following co-pending applications:

System for Monitoring Motion of a Member, U.S. Application No. 60/502,760; (LP-5345USPRV), filed Sep. 11, 2003 in the name of Chia Kuo and George W. Coulston.

Blood Pressure Monitoring System and Method, U.S. Application No. 60/502,751; (LP-5347USPRV), filed Sep. 11, 2003 in the names of George W. Coulston and Thomas A. Micka.

Reflective System for Monitoring Motion of a Member, U.S. Application No. 60/502,750; (LP-5346US PRV), filed Sep. 11, 2003 in the name of George W. Coulston;

Blood Pressure Monitoring System and Method Having Extended Optical Range, U.S. Application No. 60/526,187; (LP-5622USPRV), filed Dec. 2, 2003 in the names of George W. Coulston and Thomas A. Micka.

Extended Optical Range Reflective System for Monitoring Motion of a Member, U.S. Application No. 60/526,429; (LP-5621USPRV), filed Dec. 2, 2003 in the name of George W. Coulston.

Extended Optical Range System for Monitoring Motion of a Member, U.S. Application No. 60/526,188; (LP-5620USPRV), filed Dec. 2, 2003 in the name of Chia Kuo and George W. Coulston.

BACKGROUND OF THE INVENTION

1. Field of the Invention

This invention relates to a fabric useful in a system for monitoring motion, such as the motion generated by a geometric change in a body in response to physiological activity.

2. Description of the Prior Art

Heart rate monitors are known for measuring and reporting the heart beat of humans and animals. Such monitors receive signals from the pulsating flow of blood synchronized with the periodic pumping activity of the heart. Typically, the known monitors detect the pulsating flow of blood through a sensor in a chest belt or through a sensor clipped mechanically to an ear or finger. U.S. Pat. No. 5,820,567 (Mackie) describes a representative arrangement of a chest belt or an ear clip for a heart rate sensing apparatus.

A chest belt is difficult to fit and often requires gel to wet the sensor electrodes prior to use. Tight chest belts for heart monitoring can be uncomfortable if worn for a prolonged period. Mechanical sensors that clip to a finger or an ear can also be uncomfortable.

The QuickTouch™ heart monitor sold by Salutron Inc. (Fremont, Calif. 94538, USA) eliminates the chest strap, finger or ear clip to measure heart rate in all phases of exercise. However, while eliminating cumbersome wires and straps, two points of body contact are required in operation. This device thus requires application of two fingers on a watch band, two hands on a treadmill, or two hands on a bicycle handle bar to give heart rate readings. As a result, this device does not totally free the subject from the monitoring process.

Systems that relieve the monitored subject from the discomfort of chest belts or clip devices to the finger or ear, and from the inconvenience of being restricted to the monitoring apparatus, have been disclosed.

U.S. Pat. No. 6,360,615 (Smela) discloses a monitoring system using a garment that detects motion in the body of the wearer through a strain gauge implemented using a polypyrrole-treated fabric.

U.S. Pat. No. 6,341,504 (Istook) discloses a garment for physiological monitoring comprising one or more elongated bands of elastic material with conductive wire formed in a curved pattern. When the garment is worn by a human, the elongation and relaxation of the fabric caused by geometrical changes of the human frame induce electrical property changes in the conductive wire(s) of the garment. Such a system adds an additional component of complexity to the fabric structure, which is not well-suited to traditional garment design and construction.

U.S. Pat. No. 4,909,260 (Salem) describes a bulky waist belt system for physiological monitoring.

U.S. Pat. No. 5,577,510 (Chittum) describes bulky chest and waist belts for physiological monitoring.

Patent Publication WO 9714357, Healthcare Technology Limited, Great Britain, discloses a monitor capable of generating an audio heartbeat message.

SUMMARY OF THE INVENTION

The present invention is directed to a fabric, garment, overall system and method for monitoring motion of a member, and is believed particularly useful for monitoring motion generated by geometric changes of the body of a subject in response to physiological activity. By monitoring such motion, a noninvasive measurement of a parameter characterizing the physiological activity may be derived.

The fabric can comprise a first plurality of reflective yarns knitted or woven with a second plurality of stretchable yarns. The fabric exhibits both a light transmission property and a light reflection property when the fabric is illuminated with light having a wavelength in the range of from about 400 nanometers to about 2200 nanometers, and particularly in the ranges from about 400 to about 800 nanometers and from about 700 to about 2200 nanometers.

The amount of light transmitted through the fabric relative to the amount of light reflected by the fabric changes as the fabric stretches and recovers in response to motion, such as the motion induced geometric changes in a human body caused by physiological activity.

In the preferred instance each reflective yarn has a coating of an electrically conductive, specularly reflective material thereon, and each stretchable yarn is formed as a combination of a covered elastic yarn and a hard yarn.

The fabric may be used as a monitoring patch in a garment or textile mantle.

The garment or textile mantle having the patch of monitoring fabric disposed thereon or therein may be incorporated into a system for monitoring motion, such as the motion generated by geometric changes in the body of a subject due to physiological activity. The system further includes at least a source providing radiation with wavelength(s) in the range from about 400 nanometers to about 2200 nanometers, and particularly in the ranges from about 400 to about 800 nanometers and from about 700 to about 2200 nanometers. The system still further includes at least a detector responsive to incident radiation in the same wavelength range and subranges. The source and the detector preferably are attached to the fabric in predetermined positions such that the reception of incident radiation by the detector is directly affected by a change in the amount of radiation either transmitted through the fabric or reflected by the fabric, depending on the arrangement of the radiation source and radiation detector. Such changes occur when the fabric stretches in response to motion due to geometric changes in the body of the subject S wearing the garment or in the body component having the mantle thereon. A signal processor converts the signal received from the detector into a signal representative of at least one predetermined physiological parameter of the subject wearing the garment or mantle.

Alternatively, the system can comprise more than a single radiation source and more than a single radiation detector for each source. In such an alternative embodiment, the signal processor is responsive to signals from more than a single radiation source and more than a single radiation detector and converts these signals into a signal representative of one or more predetermined physiological parameters associated with the subject wearing the garment.

BRIEF DESCRIPTION OF THE DRAWINGS

The invention will be more fully understood from the following detailed description, taken in connection with the accompanying drawings, which form a part of this application, and in which:

FIG. 3C is a graphical representation of the change in the amount of light transmitted through the fabric relative to the amount of light reflected by the fabric as the fabric stretches (i.e., elongates and recovers);

FIG. 4B is the frequency domain spectrum of the waveform of FIG. 4A;

DETAILED DESCRIPTION OF THE INVENTION

Figure 1:
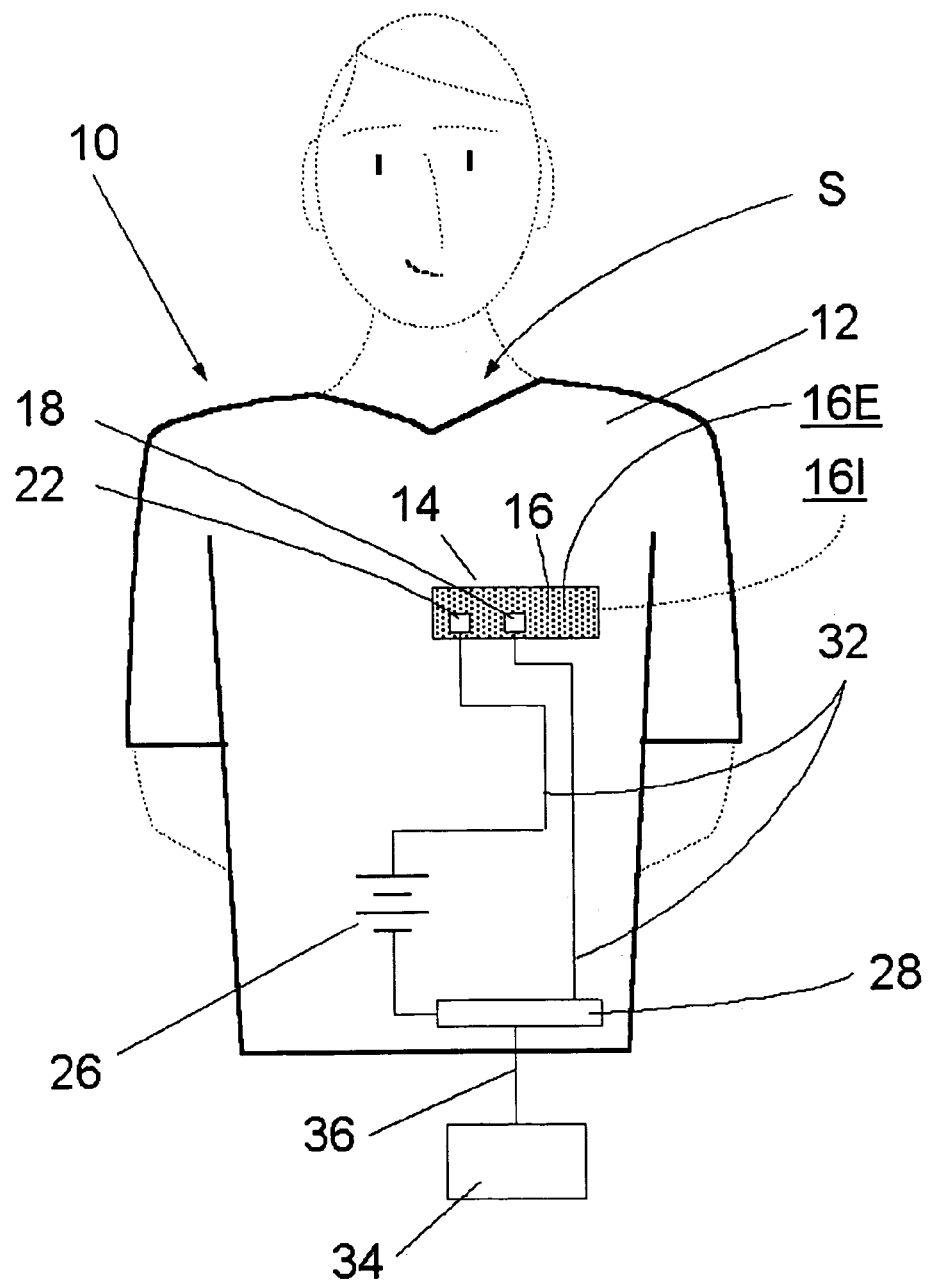
FIG. 1 is a stylized pictorial representation of a system for monitoring at least one physiological parameter of a subject S that includes a garment sized to be worn over the torso of the subject S.

Throughout the following detailed description similar reference characters refer to similar elements in all figures of the drawings.

FIG. 1 is a stylized pictorial representation of a motion monitoring system 10 in accordance with the present invention as applied to the task of monitoring motion due to geometric changes of the body of a subject S in response to physiological activity. A noninvasive measurement of one or more parameter(s) characterizing the physiological activity of the subject S may be derived by monitoring such motion(s).

As seen in FIG. 1, the system 10 includes a garment 12 having at least a portion, or patch 14, formed from a monitoring fabric 16. The monitoring fabric 16 has an exterior or outer surface 16E presented to a viewer and an interior surface 16I presented to the body of the subject S. The patch 14 of the monitoring fabric 16, although shown as rectangular in FIG. 1, may take any convenient shape. For example, the patch may be circular, oval in shape, or may be any regular or irregular shape. If desired, a portion or even the entirety of the garment 12 may be made from the monitoring fabric 16.

The monitoring fabric 16 in accordance with the present invention exhibits both a light transmission property and a light reflection property when the fabric is illuminated with light having wavelength(s) in the extended range from about 400 to about 2200 nanometers. This range is extended in the sense that it encompasses both light with wavelengths in the near infrared spectrum and broad spectrum white light having wavelengths in the visible spectrum.

As used herein the term "broad spectrum white light" means light having a wavelength in the range from about four hundred (400) nanometers to about eight hundred (800) nanometers.

As used herein the term "near infrared light" means light having a wavelength in the range from about seven hundred (700) nanometers to about twenty two hundred (2200) nanometers. The wavelength of 805 nanometers or the wavelength of 880 nanometers may be used in systems operating in the near infrared spectrum. The wavelength of 805 nanometers is preferred.

In accordance with the present invention the amount of light transmitted through the fabric 16 relative to the amount of light reflected by the fabric 16 is able to change when the fabric stretches. The stretching may be in response to geometric changes of the body of the subject S due to the occurrence of predetermined physiological activities on or within the body of the subject S, such as but not limited to, heart rate, respiration rate, blood pressure, and the like. The term "light balance" may be used herein to refer to the amount of light transmitted through the fabric 16 relative to the amount of light reflected by the fabric 16.

The monitoring fabric 16 used in the patch 14 can be made from reflective yarns, stretchable yarns or any combination of reflective and stretchable yarn or any like material. In one exemplary construction a first plurality of reflective yarns is combined with a second plurality of stretchable yarns.

The yarns can be combined in any conventional manner including woven or non-woven construction.

For woven constructions, yarns can be combined in plain weave, satin weave, twill weave or any other well known constructions. Woven fabrics may also include weft elastic, warp elastic or bielastic woven fabrics for varying fabric elasticity.

For non-woven constructions such as knit constructions, yarns can be combined by circular knit, warp knit or any other suitable knit construction. In circular knits, typical constructions are single jersey (i.e., different structure in front and back, e.g. 1×1 knit) and double jersey (i.e., same structure in front and back, e.g. 2×1 knit). The stitch size and distance determine the openness of the knit fabric. Warp knits may include tricot and raschel constructions where the tightness is determined by the number of needles/inch or the stitch size.

Any suitable apparel denier and any suitable needle combination or warp/weft intensity may be used in making the monitoring fabric. Each reflective yarn may comprise a coating of a specularly reflective material thereon. The coating may also be electrically conductive. Furthermore, the reflective yarn may be elastic or include an elastic component. Each stretchable yarn is formed as a combination of an elastic yarn component and a hard yarn component.

In the preferred instance the reflective yarn is that yarn sold by Laird Sauquoit Technologies, Inc. (300 Palm Street, Scranton, Pa., 18505) under the trademark X-static® yarn. X-static® yarn is based upon a 70 denier (77 dtex), 34 filament textured nylon available from INVISTA North America S. à r. I., Wilmington, Del. 19805, as product ID 70-XS-34X2 TEX 5Z that is electroplated with electrically-conductive silver.

Alternatively, another method of forming the monitoring fabric 16 is to screen-print a pattern using an electrically conductive ink after constructing the yarns in any conventional woven or non-woven manner. Suitable electrically conductive inks include, but are not limited to, those sold by DuPont Microcircuit Materials, Research Triangle Park, N.C. 27709, as silver ink 5021 or silver ink 5096, and the like.

A screen-printed pattern of conductive inks must also allow the fabric to move. Preferably, the conductive ink does not affect the ability of the fabric to stretch and recover. One way to prevent affecting the stretch and recovery properties of fabric is to screen-print a pattern of conductive ink(s) in the form of a matrix of dots. Such a dot matrix pattern provides full freedom of movement for the yarns in the fabric, while still exhibiting desired light reflection and transmission properties.

The patch 14 of monitoring fabric 16 can alternatively be formed from elastic and electrically conductive composite yarn comprising a core yarn made of, for instance, LYCRA® spandex yarn wrapped with insulated silver-copper metal wire obtained from ELEKTRO-FEINDRAHT AG, Escholzmatt, Switzerland, using a standard spandex covering process. The core yarn may further be covered with any nylon hard yarn or polyester hard yarn.

Stretchable yarn can be formed in any conventional manner. For example, the stretchable yarn can be formed as a combination of a covered elastic yarn and a hard yarn.

In one preferred embodiment, the covered elastic yarn can be comprised of a twenty (20) denier (22 dtex) LYCRA® spandex yarn single-covered with a ten (10) denier (11 dtex) seven filament nylon yarn. LYCRA® spandex yarn is available from INVISTA North America S. à r. I., Wilmington, Del. 19805. Alternatively, the elastic yarn component of the present invention may comprise elastane yarn or polyester bicomponent yarns such as those known as ELASTERELL-P™ from INVISTA S. à r. I. North America Inc. of Wilmington, Del. The terms spandex and elastane are used interchangeably in the art. An example of a branded spandex yarn suitable for use with the present invention is LYCRA®.

Synthetic bicomponent multifilament textile yarns may also be used to form the elastic yarn component. One preferred synthetic bicomponent filament component polymer can be thermoplastic. The synthetic bicomponent filaments can be melt spun or formed in any other manner common in the art of filament formation. In the most preferred embodiment the component polymers can be polyamides or polyesters.

A preferred class of polyamide bicomponent multifilament textile yarns comprises those nylon bicomponent yarns which are self-crimping, also called "self-texturing." These bicomponent yarns comprise a component of nylon 66 polymer or copolyamide having a first relative viscosity and a component of nylon 66 polymer or copolyamide having a second relative viscosity, wherein both components of polymer or copolyamide are in a side-by-side relationship as viewed in the cross section of the individual filament. Self-crimping nylon yarn such as that yarn sold by INVISTA North America S. à r. I., Wilmington, Del. 19805 under the trademark TACTEL® T-800™ is an especially useful bicomponent elastic yarn.

Some examples of polyester component polymers include polyethylene terephthalate (PET), polytrimethylene terephthalate (PTT) and polytetrabutylene terephthalate. In one preferred embodiment, polyester bicomponent filaments comprise a component of PET polymer and a component of PTT polymer in a side-by-side relationship as viewed in the cross section of the individual filament. One exemplary yarn having this structure is sold by INVISTA North America S. à r. I., Wilmington, Del. 19805 under the trademark T-40™ Next Generation Fiber.

The hard component could be made from any inelastic synthetic polymer fiber(s) or from natural textile fibers, such as wool, cotton, ramie, linen, rayon, silk, and the like. The synthetic polymer fibers may be continuous filament or staple yarns selected from multifilament flat yarns, partially oriented yarns, textured yarns, bicomponent yarns selected from nylon, polyester or filament yarn blends. The hard component is preferably 260 denier (286 dtex) 68 filament nylon yarn.

Nylon yarns may preferably comprise synthetic polyamide component polymers such as nylon 6, nylon 66, nylon 46, nylon 7, nylon 9, nylon 10, nylon 11, nylon 610, nylon 612, nylon 12 and mixtures and copolyamides thereof. In the case of copolyamides, especially preferred are those including nylon 66 with up to 40 mole percent of a polyadipamide wherein the aliphatic diamine component is selected from the group of diamines available from INVISTA North America S. à r. I., Wilmington, Del. 19805 (Wilmington, Del., USA, 19880) under the respective trademarks DYTEK A® and DYTEK EP®.

Further in accordance with the present invention, the hard yarn portion of the present invention may comprise polyesters such as, for example, polyethylene terephthalate, polytrimethylene terephthalate, polybutylene terephthalate and copolyesters thereof.

The monitoring fabric 16 may also be formed from composite yarns in which the reflective and stretchable components are combined in the same yarn. Such a composite yarn would include a covering yarn having a spectrally reflective outer surface that is wrapped about an elastic yarn component in one or more layers.

The remainder of the structure of the garment 12, if not also formed of the monitoring fabric, may exhibit any convenient textile construction (e.g., knitting or weaving as described above) and may be made from any suitable textile filament apparel denier yarn.

In one embodiment, the monitoring fabric 16 used in the patch 14 is attached to the garment 12. The patch 14 could be sewn, glued, stapled, taped, buttoned, interwoven or attached to the garment by any other means.

It alternatively lies within the contemplation of the invention that the garment 12 may be formed entirely from the monitoring fabric 16. Any suitable needle combination or warp/weft intensity may be used for the garment 12.

In another embodiment, the garment is seamlessly constructed of the monitoring fabric 16 using any suitable needle combination into the material of the remainder of the garment 12. In this context the term "seamless" refers to the known process of circular knitting on a seamless knitting machine (e.g., from Santoni S.p.A., Brescia, Italy). Garments processed in this way may possess minor seams, for example, the shoulder portion of a vest or the crotch seam of panty hose may be formed using traditionally practiced seaming methods. For these reasons the "seamless" term of art includes garments with one, or only a few seams, and substantially constructed from a single piece of fabric.

The system 10 shown in FIG. 1 is adapted for monitoring the motion generated by geometric changes of the body accompanying the physiological activities of respiration or heart beat of the subject S. The garment 12 is thus configured similar to a vest or shirt, although other garment configurations are contemplated. For a vest-like or shirt-like textile structure, a contour and appropriate openings are formed for disposition on the torso of the subject S. For such use, the patch 14 of monitoring fabric 16 should be located in a position of maximum sensitivity to geometric changes in the body of the subject S. For instance, the patch 14 could be used to monitor the beating heart or the chest wall movement incident with respiration by disposing the patch 14 beneath the nipple of the left breast of the subject S. It should be understood that the physical form of the garment may be appropriately modified for disposition over other parts of the body of the subject S in the event it is desired to monitor the motion of another portion of the body.

The light balance is monitored as the monitoring fabric 16 stretches and recovers. For this purpose, the system 10 further includes a suitable source 18 of radiation operable in the wavelength range from about 400 nanometers to about 2200 nanometers, and particularly in the wavelength ranges from about 400 to about 800 nanometers and from about 700 to about 2200 nanometers. An associated detector 22 is responsive to incident radiation in the given wavelength range and sub-ranges for producing signals in response thereto.

In the case of operation with near infrared light, the radiation source 18 can be a compound semiconductor-based (e.g., gallium arsenide or gallium aluminum arsenide) photo-emitting diode operating in the infrared range (at a wavelength of 805 nanometers or 880 nanometers) or any similar radiation source. The radiation detector 22 can be any device that can detect radiation, for instance, a photodiode coupled to appropriately configured output amplification stages. Any well known semiconductors can be used for forming the photodiode, including silicon or germanium. A commercially available radiation source and detector package suitable for use in the system of the present invention is that available from Fourier Systems Ltd. (9635 Huntcliff Trace, Atlanta, Ga., 30350) as model DT155 (0-5 volt output).

For broad spectrum white light (400 to 800 nanometers) operation, the source 18 can be a compound semiconductor-based "white LED" (e.g., a light emitting diode employing an indium gallium nitride based device with suitable phosphors to provide broad spectrum white light emission). The detector 22 is preferably a silicon phototransistor coupled to appropriately configured output amplification stages.

The radiation source 18 and the detector 22 are attached to monitoring fabric 16 in predetermined relative positions. The positions were determined such that the reception of incident radiation by the detector 22 is directly affected by a change in the amount of light transmitted through the monitoring fabric 16 relative to the amount of light reflected by the monitoring fabric 16 when the fabric stretches and recovers. In the preferred case, the radiation source 18 and detector 22 are embedded, or fixed firmly, into the textile structure of the monitoring fabric 16. The radiation source 18 and detector 22 can be fixed using any well known attachment method, including but not limited to, clamping, gluing, sewing, taping, or hook and loop fasteners (Velcro). Optionally, it may be desirable in some operational configurations of the invention (e.g., when the subject S is on a treadmill) to dispose both the source and the detector remote from and not in direct contact with the fabric 16. In such a remote arrangement, the radiation source 18 and detector 22 could be located in any arrangement that permits the detector 22 to detect changes in the transmission and reflection of radiation during stretching and recovery.

In the operational configuration shown in FIG. 1 (and discussed more fully in connection with FIGS. 2A and 2B) both the source 18 and the detector 22 are mounted to the exterior surface 16E of the patch 14 of monitoring fabric 16. Alternatively, as discussed in connection with FIGS. 3A and 3B, one of the source 18 or the detector 22 is mounted to the exterior surface 16E of the patch 14 of monitoring fabric 16 while the other of the detector 22 or the source 18 is mounted to the interior surface 16I of the patch 14 of the monitoring fabric 16.

A suitable electrical source 26 for the radiation source 18 may be conveniently carried in the garment 12. The electrical source 26 can be any conventional electrical source known in the art including, but not limited to, a battery.

The system 10 may further comprise a signal acquisition and storage unit 28 coupled to the detector 22 for storing signals produced thereby in response to incident radiation. Electrically conductive paths 32 are provided in the garment 12 to interconnect the infrared source 18, the detector 22, the electrical source 26 and the signal storage unit 28 in any appropriate electrical configuration.

One convenient manner of forming the conductive paths 32 is to knit or weave conductive filaments into the garment 12. A suitable conductive filament for such use is the X-static® yarn mentioned earlier. Alternatively, the wires could be arranged so as to be unattached to the fabric.

Another method of forming the conductive paths 32 is to screen-print the pattern of conductive paths using an electrically conductive ink. Any conductive ink could be used including, for instance, electrically conductive inks sold by DuPont Microcircuit Materials, Research Triangle Park, N.C. 27709, as silver ink 5021 or silver ink 5096. Silver ink 5021 ink is useful in fabricating low voltage circuitry on flexible substrates, while silver ink 5096 is suggested for use in situations where extreme crease conditions are encountered. While silver ink 5021 has a higher conductivity, silver ink 5096 is more easily spread and more easily builds bridges among the fibers of the fabric of the garment 12.

Once the signal is received by the radiation detector 22, a signal processor 34 may be used to convert the periodically varying signal output from the detector 22 representative of incident radiation thereon into a signal representative of at least one (or a plurality) of predetermined parameter(s) (e.g., respiration rate, heart rate) of the subject S wearing the garment 12. In the preferred instance the signal processor 34 comprises a suitably programmed digital computer. However, any signal processor known to those skilled in the art could be used.

The signals from the detector 22 stored within the storage unit 28 may be transferred to the signal processor 34 in any convenient manner for conversion into signals representative of the physiological parameter(s) of the subject S. For example, transfer between the storage unit 28 and the processor 34 may be effected by either a hardwired connection or a through-space wireless (e.g., a wireless LAN using 2.4 GHz and 802.11a/b or 802.11g protocol known to skilled practitioners of the wireless high speed data communications) or an optical transmission link, as suggested in the area indicated by reference character 36 in FIG. 1.

The signal from detector 22 is a raw signal and comprises a composite of frequencies containing at least the respiration cycle and heart rate of the subject S. Certain noise sources contribute to the overall waveform. Such noise sources are believed to arise from extraneous motion of the subject S or the monitoring fabric 16 and are not associated with respiration and heart rate. These sources of noise could be filtered using appropriate electronic filtering techniques. Specifically, high frequency and low frequency pass filters appropriately chosen can create a cleaner raw overall waveform. Such filters could be selected according to methods known to those skilled in the art in order to obtain a signal associated only with respiration or one associated only with heartbeat. Equivalently, filters to reduce known sources of signal noise are also easily employed in the data acquisition system.

Although the signal processor 34 illustrated in FIG. 1 is disposed at a location remote from the garment, it should be understood that it lies within the contemplation of the invention to implement the processor in a suitably sized package able to be physically mounted on the garment. In such an instance the output from the detector 22 may be directly buffered into appropriate memory within the processor 34.

The operation of the motion monitoring system of the present invention in the reflection mode may be more clearly understood with reference to FIGS. 2A through 2D. As noted earlier, in the reflection mode of operation both the source 18 and the detector 22 are mounted on or adjacent to the same surface of the monitoring fabric 16, typically the exterior surface 16E.

The source 18 is arranged in such a way as to maintain its relative position to the detector 22. For instance, the source 18 and detector 22 may be rigidly connected together on one side of the monitoring fabric 16 to maintain a spatial relationship. Alternatively, the position of the source relative to the detector can be maintained on opposite sides of the monitoring fabric 16 for monitoring transmission. In such an embodiment, the radiation source 18 is connected to the radiation detector 22 using a "clothes-pin" or alligator style clamp. Any well known means of maintaining the spatial relationship of the source 18 relative to the detector 22 could be used.

Figure 2A:
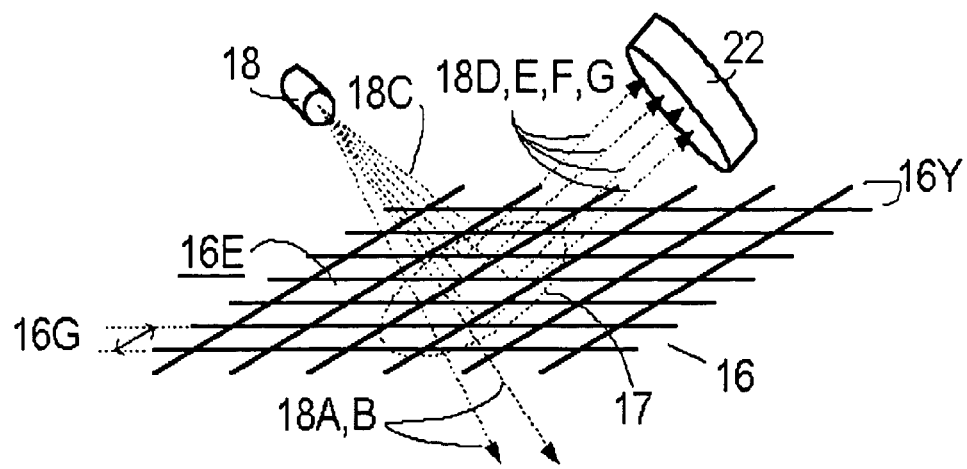
FIGS. 2A and 2B are diagrammatic views illustrating the operation of the monitoring system of the present invention when operating in the light reflection mode.
Figure 2B:
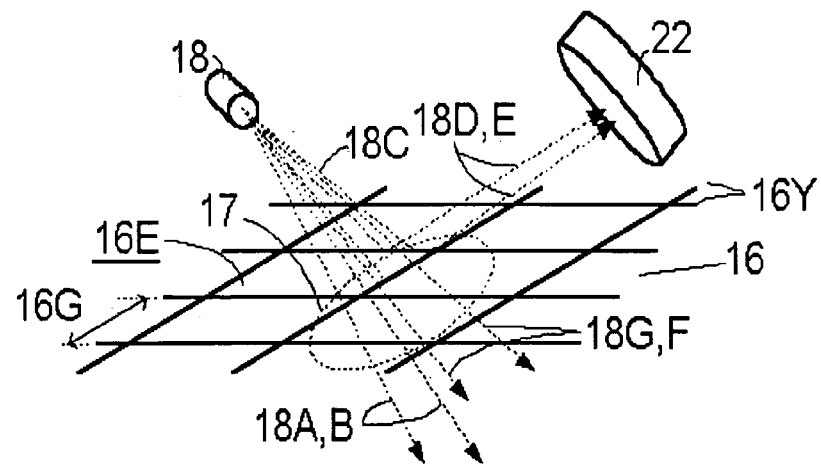

The operation is discussed in the context of monitoring the periodic physiological activity of respiration. FIG. 2A illustrates the fabric 16 in an unstretched state, while FIG. 2B illustrates the fabric 16 in a stretched state. The stretching illustrated in FIG. 2B can be caused by movements such as the periodic physiological activity of respiration. It should be noted that FIGS. 2A and 2B are schematic and are not drawn to scale. For instance, though only two dimensional movement of the fabric is shown, movement in all directions is contemplated. As discussed above, any extraneous motions of the subject S or monitoring fabric 16 could be filtered as noise using appropriate electronic filtering techniques.

As represented in FIG. 2A, in the unstretched state the filaments forming the yarns 16Y of the monitoring fabric 16 lie within a relatively close distance of each other to define a pattern of relatively narrow gaps 16G. A generally circular spot indicated by the reference character 17 represents the area of the monitoring fabric 16 illuminated by the source 18. Using appropriate optics (e.g., an objective lens on the source 18) the size of the spot 17 may be adjustably selectable to focus on an area containing any arbitrary number of yarns 16Y forming the fabric 16 or down to an area containing only a single filament of a yarn 16Y.

The radiation detector 22 can be arranged on the same side of the monitoring fabric 16 to receive radiation (so called "reflection mode") or the detector 22 can be arranged to on the opposite side of the monitoring fabric 16 to receive transmitted radiation (so called "transmission mode"). Of the photons emitted from the source 18 toward the surface 16E of the fabric 16, some photons are absorbed (e.g., represented by a ray 18C) by the filaments 16F of the fabric while other photons (e.g., the rays 18A and 18B) pass through gaps 16G therein. All of these photons (18A, 18B, 18C) are lost to the detector 22 if the source 18 and detector 22 are arranged in reflection mode. In such an arrangement, the major portion of the light (e.g., represented by the rays 18D through 18G) is reflected from the surface 16E of the monitoring fabric 16 toward the detector 22 when the fabric is not stretched. This major portion of the light is useful in producing a corresponding output signal from the detector 22.

As seen from FIG. 2B, as the fabric stretches, the size of the gaps 16G formed in the monitoring fabric 16 increases. This increase in size of the gaps 16G increases the likelihood that a photon will pass through the fabric 16 (and be lost to the detector arranged in reflection mode), and decreases the likelihood that a photon will usefully reflect toward the detector 22. The total number of photons lost to the detector 22 by transmission through the fabric (e.g., represented by the rays 18A, 18B, 18G and 18F) increases and the signal output from the detector 22 in reflective mode concomitantly decreases. Although the number of photons absorbed (e.g., represented by the ray 18C) does not necessarily change, the amount of yarn 16Y within the spot size 17 decreases, and it becomes less likely that a photon will strike yarn 16Y and be reflected or absorbed.

As the body of the subject S contracts during an exhalation, the fabric 16 undergoes the elastic recovery phase of its stretch. The gaps 16G return to their original size (FIG. 2A). A relatively large portion of the light is again usefully reflected toward the detector 22, increasing the output signal therefrom.

Figure 2C:
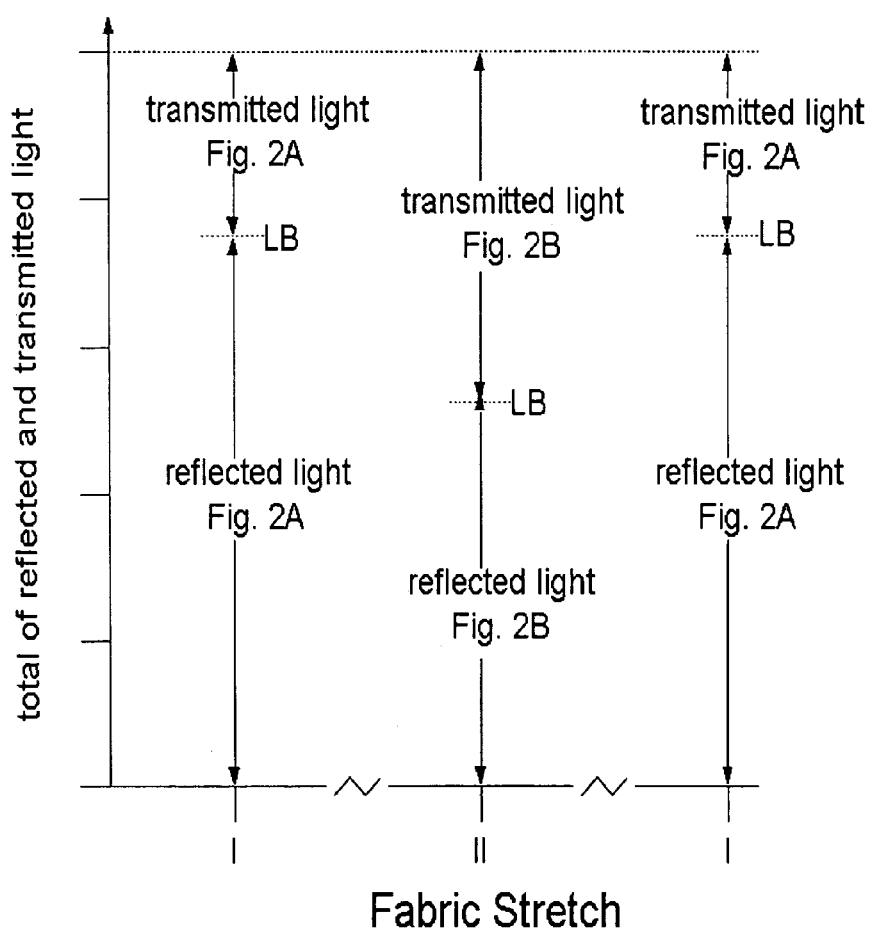
FIG. 2C is a graphical representation of the change in the amount of light transmitted through a fabric relative to the amount of light reflected by the fabric as the fabric stretches and recovers.

Viewed consecutively these events define a stretch cycle of elongation and recovery. The signal generated at the detector 22 of the monitoring system varies from an initial state to an intermediate state and back to the initial state, as represented by FIG. 2C. This figure graphically illustrates that during the course of a stretch cycle the light balance (reference character "LB" in FIG. 2C) of the fabric changes. Comparison between the initial and inhalation states (indicated by respective reference characters "I" and "II" in FIG. 2C) and between the inhalation and exhalation states (indicated by respective reference characters "II" and back to "I" in FIG. 2C) clearly shows that the amount of light reflected by the monitoring fabric 16 changes in a periodic fashion over time as the fabric stretches. In FIG. 2C, at the initial state ("I") the reflected light represented by the bottom portion below the "LB" is greater than the transmitted light represented by the upper portion above the "LB". In contrast, at the inhalation state ("II") the reflected light represented by the bottom portion below the "LB" is less than the transmitted light represented by the upper portion above the "LB".

Figure 2D:
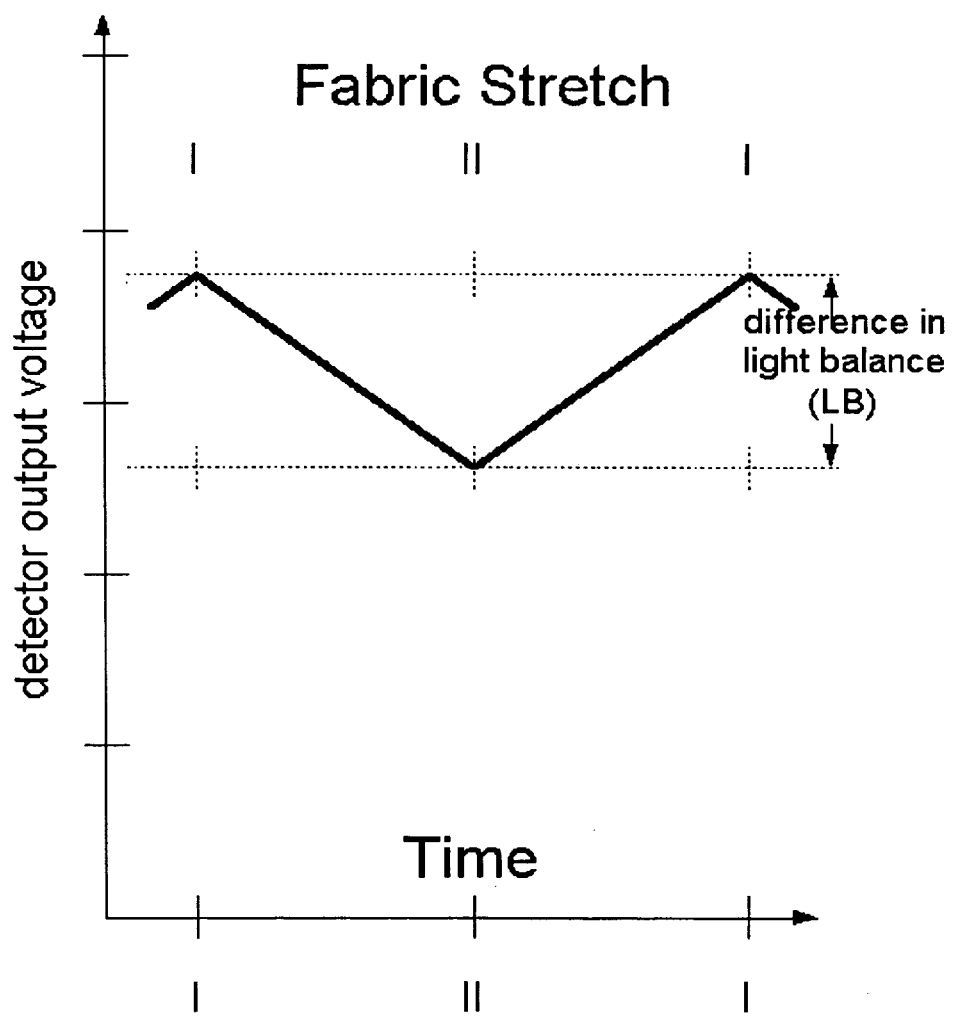
FIG. 2D is a graphical representation of a signal, periodic in time, representing the change in the amount of light transmitted through the fabric relative to the amount of light reflected by the fabric during stretching and recovery of the fabric.

This periodic variation in light balance is represented by FIG. 2D as a time-varying signal from "I" to "II" to "I" synchronized with the elongation and recovery stages of fabric stretch. This signal can be a temporal measure of the underlying physiological processes, which provide the forces causing the elongation and recovery.

Figure 3A:
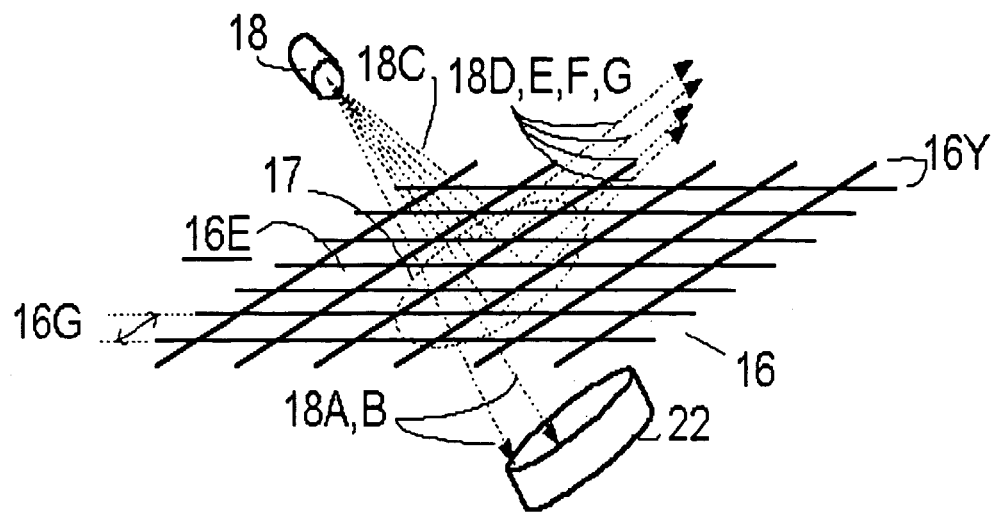
FIGS. 3A and 3B are diagrammatic views illustrating the operation of the monitoring system of the present invention when operating in the light transmission mode.
Figure 3B:
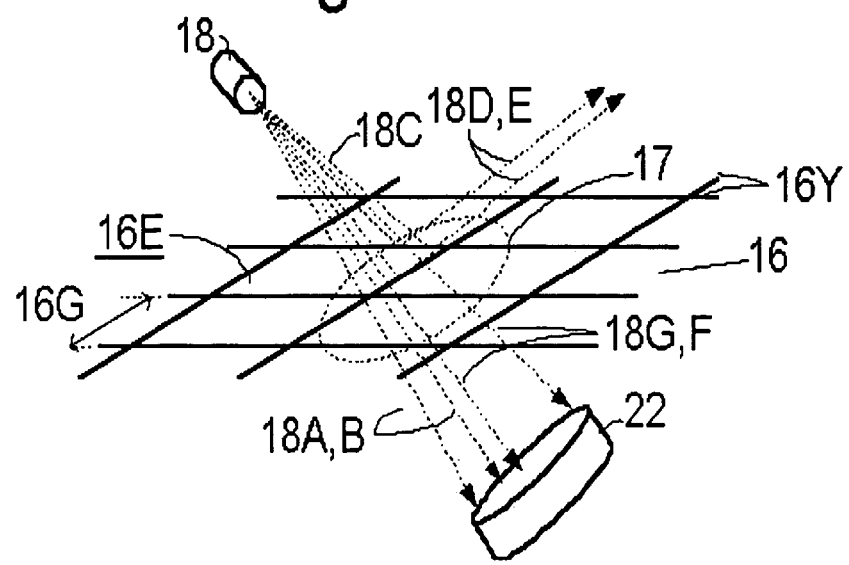

Alternatively, the system 10 may operate in a light transmission mode as represented by FIGS. 3A, 3B. As in FIGS. 2A and 2B, the illustrations are schematic and are not drawn to scale. In the transmission mode of operation the source 18 and the detector 22 are disposed on opposite sides of the monitoring fabric 16. The operation is again discussed in the context of monitoring respiration.

When the fabric 16 is not stretched (FIG. 3A), only a relatively small portion of the light from the source 18 illuminating the spot 17 passes through gaps 16G in the fabric 16. As a result the number of photons (e.g., represented by rays 18A and 18B) incident on the detector 22 and useful to produce a signal therefrom is concomitantly low. Photons reflected from the fabric 16 (e.g., represented by the rays 18D through 18G) or photons absorbed by the fabric filaments 16F (e.g., represented by the ray 18C) are lost, and thus contribute nothing to the output of the detector 22.

However, when the fabric 16 elongates due to motion in the body of the subject S during an inhalation (as represented in FIG. 3B) the number of photons transmitted through the gaps 16G in the fabric increases (e.g., represented by the rays 18A, 18B, 18G and 18F) since the illumination spot size 17 remains constant. This increase in the number of useful photons falling upon the detector 22 changes its output accordingly. Some of the photons from source 18 are reflected (e.g., represented by the rays 18D and 18E) or absorbed (e.g. represented by the ray 18C) and are lost, and so contribute nothing to the output of the detector 22.

The change in light balance LB is graphically represented in FIG. 3C. Again, for simplicity of discussion the portion of the total light budget absorbed by the fabric is ignored.

As represented by FIG. 3C the signal generated at the detector 22 varies from an initial state to an intermediate state and back to the initial state as the fabric undergoes a stretch cycle of elongation from an initial state followed by recovery. The change in light balance of the fabric during the course of a stretch cycle is again graphically illustrated in FIG. 3C. Comparison between the initial and inhalation states (indicated by respective reference characters "I" and "II" in FIG. 3C) and between the inhalation and exhalation states (indicated by respective reference characters "II" and back to "I" in FIG. 3C) clearly shows that the amount of light transmitted through the fabric 16 relative to the amount of light reflected by the fabric 16 changes in a periodic fashion over time as the fabric stretches. (In the transmission mode case, light lost to the detector due to absorption contributes to the "reflected light" section of the graph.) Thus, in FIG. 3C in the initial state ("I") the reflected light represented by the bottom portion below the "LB" is greater than the transmitted light above the "LB", and in the inhalation state ("II"), the reflected light represented by the bottom portion below the "LB" is less than the transmitted light above the "LB".

Figure 3D:
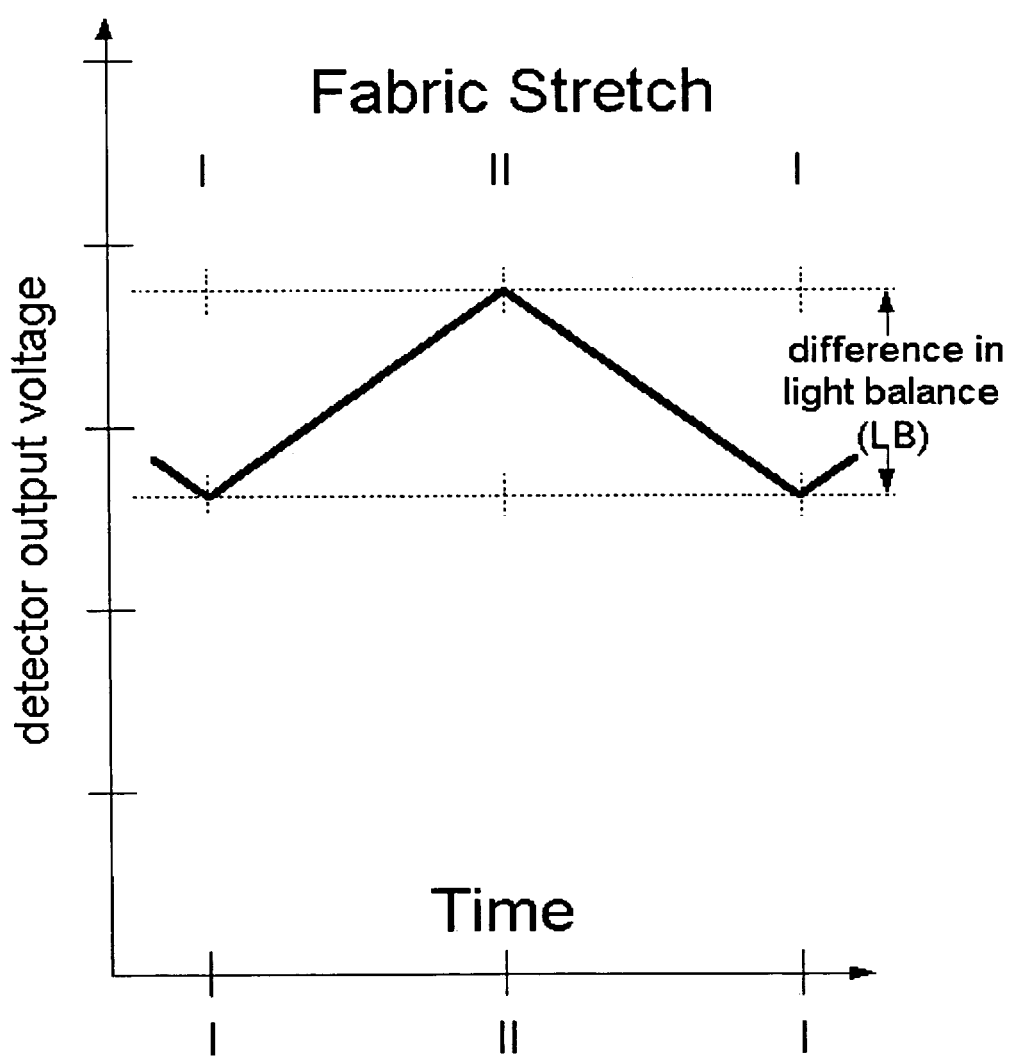
FIG. 3D is a graphical representation of a signal, periodic in time, representing the change in the amount of light transmitted through the fabric relative to the amount of light reflected by the fabric during stretching cycles (consecutive elongation and recovery) of the fabric.

This periodic variation in light balance is represented by FIG. 3D as a time-varying signal from "I" to "II" to "I" synchronized with the elongation and recovery stages of fabric stretch, and provides a temporal measure of the underlying physiological processes which provide the forces causing the elongation and recovery.

As in the case of the signal of FIG. 2C, this signal representing the change in light balance LB is used to derive a signal representative of the physiological parameter of a subject S wearing the garment 12.

Those skilled in the art will also recognize that the principles underlying the invention as heretofore described can be applied in a variety of other situations where it is desired to monitor the motion of a member. For example, in another embodiment the motion monitoring system of the present invention may be used to monitor movement of a component of a multicomponent structure.

The motion monitoring system for such a usage comprises a textile mantle, at least a portion of which is formed from the monitoring fabric. The term "textile mantle" encompasses any fabric structure covering (in whole or in part) a component of a structure.

The textile mantle is disposed in any convenient manner over the component whose motion is to be monitored. In the same way as heretofore discussed the source 18 and a detector 22 are attached to the textile mantle in relative positions such that the reception of incident radiation by the detector 22 is directly affected by a change in the amount of light transmitted through the fabric 16 relative to the amount of light reflected by the fabric 16 when the fabric 16 undergoes a stretch cycle in response to motion of the component.

EXAMPLES OF THE INVENTION

Example 1

A garment 12 substantially as depicted in FIG. 1 was constructed to demonstrate the principles of the invention. The garment 12 having an integral patch 14 of monitoring fabric 16 was constructed using a eight-feed circular knitting machine, such as a Santoni SM8-8TOP. The patch 14 was located just below the left nipple on the chest. The monitoring fabric 16 defining the patch portion 14 was constructed using four ends of reflective conductive yarns and four ends of a stretchable yarn. Each end of reflective conductive yarn was an X-Static® yarn as described earlier. Each end of stretchable yarn was formed as a combination of a soft component and a hard component. The soft component comprised a twenty (20) denier (22 dtex) LYCRA® spandex yarn single-covered with a ten (10) denier (11 dtex) seven filament nylon yarn. The hard component comprised a 260 denier (286 dtex) 68 filament nylon yarn. The remainder of the garment 12 was constructed of covered LYCRA® spandex yarn and nylon combination yarns supplied to all eight feeds of the circular knitting machine; no reflective yarn was fed to the machine. The knitting machine speed was forty-nine (49) revolutions per minute, and the garment was produced directly in wearable form.

The source 18 and detector 22 were arrayed in the transmission mode as depicted in FIGS. 3A and 3B. The source 18 and the detector 22 were configured using the single package acquired from Fourier Systems Ltd. (9635 Huntcliff Trace, Atlanta, Ga., 30350) as DT155 with an output of zero to five (0-5) volts. The wavelength used was 805 nanometers.

The DT155 source/detector package was clipped directly to the patch 14. The output from the detector 22 was directed to a signal acquisition unit acquired from Fourier Systems Ltd. known as the "MultiLogPro". This signal acquisition unit included an on-board battery package. The data acquisition unit included user-selectable detector signal sampling rate in order to best resolve the frequencies expected, i.e., the rate of the heart beat and the rate of the respiration of the subject. Since the expected frequencies were in the range of one hundred Hz or less, a signal sampling rate of fifty (50) Hz was selected.

The zero to five volts output signal from data acquisition unit was downloaded to a C600 laptop computer with a Mobile Pentium® III CPU, 750 MHz, available from Dell Computer for signal processing.

Figure 4A:
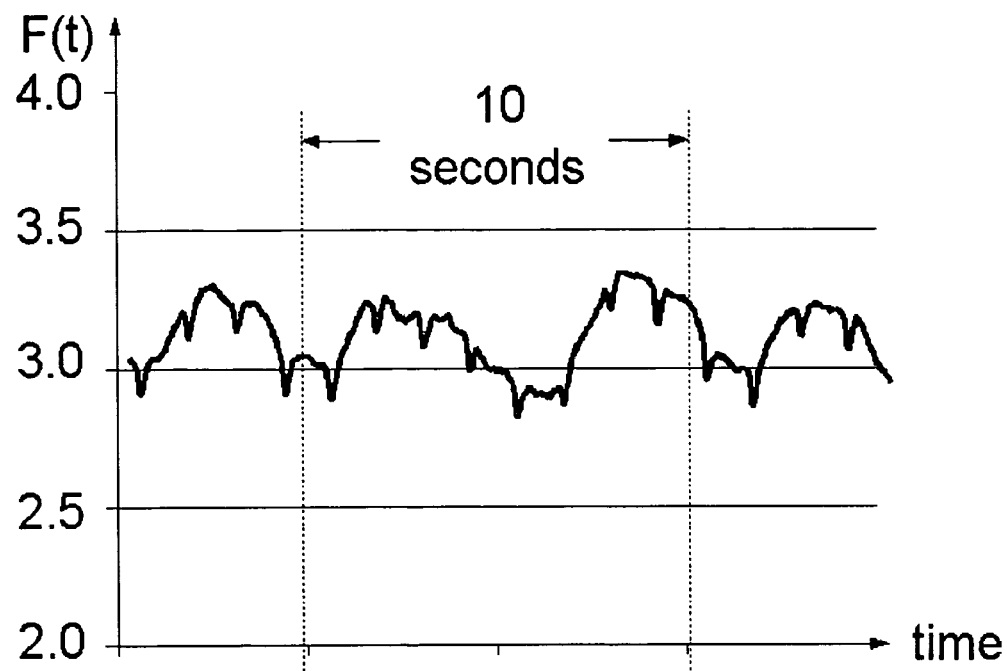
FIG. 4A is a time diagram of the waveform of the raw signal produced by the described Example of the invention.

A raw signal obtained from a subject S is shown in FIG. 4A. This signal is a composite of frequencies containing at least the respiration cycle and heart rate of the subject S. Certain noise sources contribute to the overall waveform. Such noise sources are believed to arise from extraneous motion of the subject S and fabric 16 and are not associated with respiration and heart rate. These sources of noise could be filtered using appropriate electronic filtering techniques. Specifically, high frequency and low frequency pass filters appropriately chosen can create a cleaner raw overall waveform. Such filters could be selected accordingly by methods known to those skilled in the art in order to obtain a signal associated only with respiration or one associated only with heartbeat. Equivalently, filters to reduce known sources of signal noise are also easily employed in the data acquisition system.

The composite frequency waveform of FIG. 4A is resolvable into the frequency domain spectrum shown in FIG. 4B by methods known to those skilled in the art. In this example the raw signal of FIG. 4A was downloaded to a computer and processed using a Fourier frequency deconvolution algorithm.

The raw data of FIG. 4A [F(time) versus time] was expressed as in Equation 1.

$$F(t) = a_0 + a_n \sum_{n=1}^{\infty} \sin(2\pi nft) \quad (1)$$

where $a_n$ reflects the relative magnitude of those signal components with frequency n (per minute) and $a_0$ is zero frequency ("DC") component.

The relative amounts of each expected frequency in the spectrum is given by weighting coefficients ($a_n$) determined from Equation 2.

$$a_n = (2/L) \int_0^L F(t)\sin(2\pi nft)\,dt \quad (2)$$

where L is a parameter affecting the frequency resolution to be achieved and selected by known methods.

In this case, the base frequency or lowest frequency (f) to be expected was chosen as one per minute. Any frequency greater than the base frequency (nf; where n is an integer) was resolvable as a consequence.

Figure 4C:
FIGS. 4C and 4D are waveforms representative of physiological parameters of the subject derived from the waveform of FIG. 4A.
Figure 4D:

Two predominating frequencies were found using these methods. These results are represented by FIGS. 4C and 4D. FIG. 4C is the heart beat rate of 78 per minute, and FIG. 4D is the breathing rate of 18 per minute.

This result illustrates that a garment having a portion of monitoring fabric strategically located thereon can successfully report the breathing (respiration) rate and heart rate of the garment wearer where the garment functions as part of a system according to the disclosures herein.

The fabric used in this example was monitored using the DT155 source and detector package attached to this fabric in the transmission mode of operation. The source and detector package had a zero to 5 volt range. The output from the detector was measured as a function of the fabric elongation in three discrete stages: relaxed; elongated by ten percent greater than the relaxed state (ten percent stretch); and elongated by twenty percent greater than the unstretched state (twenty percent stretch).

The measured detector voltage was the complement of the reflection plus the absorption by the fabric. As a result, an increase in light transmission with increasing fabric elongation provided a decreasing voltage. In the initial state the voltage was 3.64 volts (this output may be called the fabric bias voltage). At ten percent elongation, the voltage was 3.36 volts, and at twenty percent elongation, the output was 2.71 volts.

Figure 4E:
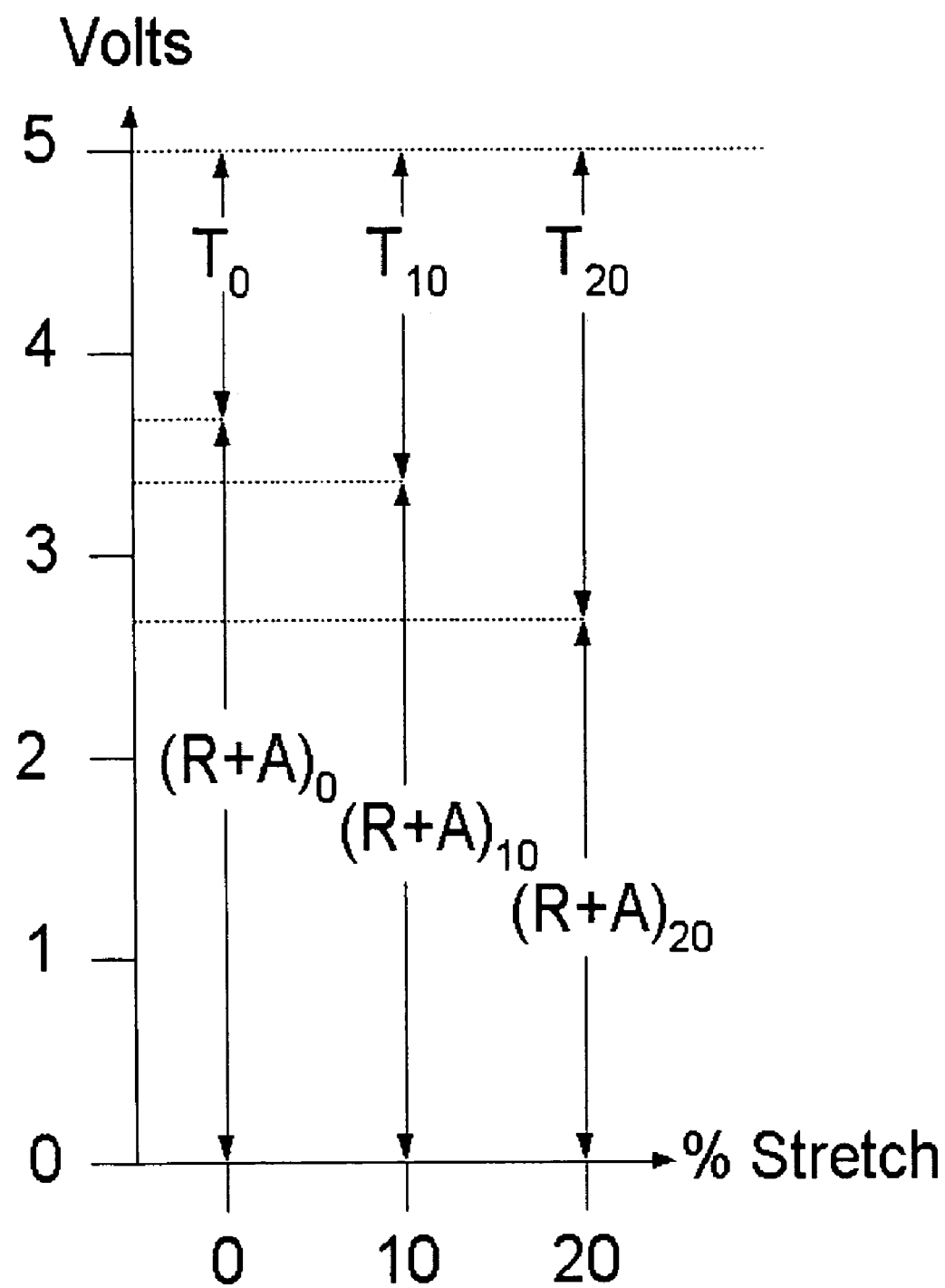
FIG. 4E is a graphical representation of the amount of light transmitted through a fabric relative to the amount of light reflected by the fabric in each of three discrete elongation stages of fabric stretch.

These results are graphically represented by FIG. 4E. FIG. 4E illustrates that the amount of light transmitted through the monitoring fabric relative to the amount of light reflected by the monitoring fabric (i.e., the light balance) changes when the fabric stretches in response to motion.

Any program can be used to deconvolute the Fourier frequency. A program, written in Visual Basic language, useful for performing a Fourier frequency deconvolution is as follows:

```
Sub find_an( )
'
' findheartbeat Macro
L = Cells(9, 7).Value
    f = Cells(9, 5).Value
    j = 12
        avg = Cells(12, 5).Value
' avg = 0
    For n = 1 To 95
    an = 0
    bn = 0
    i = 4
kuo2: t1 = Cells(i, 1).Value
    t2 = Cells(i + 1, 1).Value
    y1 = Cells(i, 2).Value – avg
    y2 = Cells(i + 1, 2).Value – avg
        an = an + 2/L * (y1 * Sin(2 * 3.1416 * n * f * t1) +
        y2 * Sin(2 * 3.1416 *
    n * f * t2))/2 * (t2 – t1)
        bn = bn + y1 + avg
        If t2 > L Then
        GoTo kuo1
        Else
        i = i + 1
        GoTo kuo2
        End If
kuo1: Cells(j + n, 5).Value = an
    Next n
End Sub
```

Example 2

In this example, Example 1 was repeated substantially in the same manner, except for the use of a source providing radiation at the wavelength of 880 nanometers. Substantially the same result was achieved.

Example 3

Except for the following changes, Example 1 was repeated substantially in the same manner. A source (broad spectrum white light LED; a suitable source is available from Lumitex® Inc., 8443 Dow Circle, Strongsville, Ohio 44136, USA; Part No. 003387) providing radiation in the wavelength range of 430 to 700 nanometers was used in combination with a silicon phototransistor detector and suitable amplification circuitry commonly employed in the art. A combined respiration and heart rate signal was obtained. However, in this example the signal was not further processed, as in Example 1, to separately obtain heart and respiration rates.

Example 4

In this example, fabrics of different types and construction were monitored using the DT155 source/detector package (with a zero to 5 volt range) attached to the fabric in the transmission mode of operation exactly as in Example 1 of the invention. The output from the detector was measured with the fabric in an unstretched condition, also called the static fabric state. As before, the measured detector voltage was the complement of the reflection plus the absorption by the fabric.

In each measurement the static fabric state was characterized with a voltage signal from the detector. This output was called the fabric bias voltage. A zero bias voltage meant total fabric transmission for the 805 nanometer light from the source.

Simultaneously with the bias voltage measurement, a DT009 light sensor obtained from Fourier Systems Ltd. coupled with the "MultiLogPro" (as in Example 1) was used to measure visible light transmission through the fabric. This light transmission was measured as illuminance with a direct output in LUX (one LUX=one lumen per square meter). The illuminance measurement with the DT009 light sensor measured light transmission of the fabric samples from a standard fluorescent desk lamp, which provided light with wavelengths mostly in the spectral range from 440 to 550 nanometers. The measured illuminance from the standard fluorescent desk lamp was 400 LUX incident on each sample. The illuminance (LUX) transmitted by the fabric was a measure of the openness of each sample. The data is reported in Table 1 below.

As is seen in Table 1, fabrics of different construction, composition and thickness provide a range of visible light transmission and light balance (transmission, absorption and reflection) for light with an 805 nm wavelength. A workable light balance can be achieved using a single fabric layer, and will yield a good bias voltage, e.g. in the range of 2.5 to 3.5 volts, in the static fabric state. The X-Static® yarn patch in a single layer of 1×1 knit fabric is one exemplary fabric that yields excellent results. The X-Static® yarn 1×1 knit patch in a single layer shows a 6.45 LUX visible light transmission and a bias of 3.17 volts. Table 1 sets out various fabrics tested and the corresponding illuminance and bias voltage observed.

TABLE 1

| Fabric/garment sample | description | Illuminance transmitted (LUX) static | Bias voltage in static condition |
|---|---|---|---|
| Example 1 shirt outside reflective X-Static ® yarn patch | One layer, 0.023 inch thickness | 177.0 | 0.0 |
| Polyester woven fabric | 2GT, no dye, one layer thick | 165.0 | 0.0 |
| Tommy Jeans ® tee shirt | 100% cotton, one layer | 163.0 | 0.0 |
| LYCRA ® nylon fabric | Knit, one layer | 149.0 | 0.0 |
| Polyester woven fabric | 2GT, no dye, two layers thick | 109.0 | 0.0 |
| Tommy Jeans ® tee shirt | 100% cotton, two layers | 84.0 | 0.0 |
| LYCRA ® nylon fabric | Knit, two layers | 74.0 | 0.0 |
| LYCRA ® nylon fabric | Knit, one layer, conductive ink coated | 72.0 | 2.88 |
| Example 1 shirt outside reflective X-Static ® yarn patch | four layers, 0.092 inch thickness | 45.0 | 0.0 |
| Example 1 shirt outside reflective X-Static ® yarn patch | eight layers | 16.4 | 1.50 |
| Polyester woven fabric | 2GT, woven, no dye, eight layers thick | 16.0 | 1.36 |

TABLE 1-continued

| Fabric/garment sample | description | Illuminance transmitted (LUX) static | Bias voltage in static condition |
|---|---|---|---|
| LYCRA ® nylon fabric | Knit, eight layers | 9.67 | 0.0 |
| Example 1 shirt inside reflective X-Static ® yarn patch | 1 × 1 Knit, one layer | 6.45 | 3.17 |
| LYCRA ® nylon fabric | Knit, 16 layers | 2.34 | 3.50 |
| Example 1 shirt inside reflective X-Static ® yarn patch | 2 × 1 Knit, one layer | 0.88 | 3.77 |
| Example 1 shirt inside reflective X-Static ® yarn patch | 2 × 1 Knit, two layers | 0.58 | 3.89 |
| Example 1 shirt inside reflective X-Static ® yarn patch | 1 × 1 Knit, two layers | 0.29 | 3.96 |
| Example 1 shirt inside reflective X-Static ® yarn patch | 2 × 1 Knit, 4 layers | 0.29 | 3.90 |
| Example 1 shirt inside reflective X-Static ® yarn patch | 1 × 1 Knit, 4 layers | 0.0 | 3.85 |

It may be appreciated from the foregoing that the fabric, garment and system of the present invention provides a particularly useful noninvasive technique for the monitoring of one or more physiological parameters of a subject without necessitating a change of clothing or the use of a chest or body strap or clamp. However, the fabric and system of the present invention also allow for the monitoring of any movement that can be translated into the elongation and recovery of elastic monitoring material.

When the fabric is in use, as when incorporated into a garment or mantle, the stretch cycle of elongation and retraction of the fabric in response to physiological activity of a subject wearing the garment or a component having the mantle thereon changes, or modulates, the amount of light transmitted through the fabric relative to the amount of light reflected by the monitoring fabric.

Those skilled in the art, having the benefit of the teachings of the present invention as hereinabove set forth, may effect modifications thereto. Such modifications are to be construed as lying within the scope of the present invention, as defined by the appended claims.

What is claimed is:

1. A system for monitoring at least one predetermined physiological parameter of a wearer, comprising:
 a garment, at least a portion of which garment is formed from a fabric having a first side defining an exterior surface and having a second side defining a wearer-contacting interior surface when said garment is worn by the wearer, wherein the fabric comprises a first plurality of reflective yarns knitted or woven with a second plurality of stretchable yarns, wherein each reflective yarn has a coating of an electrically conductive material thereon and each stretchable yarn is formed as a combination of a covered elastic yarn and a hard yarn, said fabric having a region thereof defining gaps of a first size between yarns when said fabric is stretched and defining gaps of a second size between yarns that is different from said first size when the fabric recovers from stretch;

at least one source of radiation having wavelength(s) in the range from about 400 to about 2200 nanometers positioned external to the fabric to direct radiation onto the exterior surface and onto the region;

at least one detector responsive to incident radiation having wavelength(s) in the range from about 400 to about 2200 nanometers, to produce a signal representative thereof, with said detector mounted to either the first side or the second side of the fabric and external to the fabric, wherein the source and detector are associated with the fabric in substantially fixed relative positions with respect to the region such that the reception of incident radiation by the detector at a first time interval when the fabric is stretched as compared to the reception of incident radiation by the detector at a second time interval when the fabric recovers from stretch is directly affected by a change in the amount of light reflected by yarns or transmitted through the gaps as the fabric of the region periodically stretches and recovers from stretch in response to at least one predetermined physiological parameter of the wearer of the garment; and a signal processor that converts periodically varying signal output received from the detector or from a data acquisition unit associated with the detector into a signal representative of the at least one predetermined physiological parameter of the wearer of the garment.

2. The monitoring system of claim 1 wherein the source and the detector are mounted on opposing sides of the fabric.

3. The monitoring system of claim 1 wherein the source and the detector are mounted on a same side of the fabric.

4. A system for monitoring motion of a structure, the structure comprising at least a first component, the system comprising:

a textile mantle mounted to the at least first component, at least a portion of which is formed from a fabric having a first side defining an exterior surface and having a second side defining a component-contacting interior surface when said mantle is mounted to the first component, said fabric comprising a first plurality of reflective yarns knitted or woven with a second plurality of stretchable yarns, wherein each reflective yarn has a coating of an electrically conductive material thereon and wherein each stretchable yarn is formed as a combination of a covered elastic yarn and a hard yarn, said fabric having a region thereof defining gaps of a first size between yarns when said fabric is stretched and defining gaps of a second size between yarns that is different from said first size when the fabric recovers from stretch;

at least one source of radiation having wavelength(s) in the range from about 400 to about 2200 nanometers positioned external to the fabric to direct radiation onto the exterior surface and onto the region;

at least one detector responsive to incident radiation having wavelength(s) in the range from about 400 to about 2200 nanometers to produce a signal representative thereof, said detector being mounted to either the first side or the second side of the fabric and external to the fabric, the at least one source and detector being attached to the textile mantle in relative positions with respect to the region such that the reception of incident radiation by the detector at a first time interval when the fabric is stretched as compared to the reception of incident radiation by the detector at a second time interval when the fabric recovers from stretch is directly affected by a change in the amount of light transmitted through the gaps as the fabric of the region periodically stretches and recovers from stretch in response to motion of the component; and a signal processor that converts periodically varying signal output received from the detector or from a data acquisition unit associated with the detector into a signal representative of the motion of the first component.

5. The system of claim 1 wherein the fabric exhibits the light transmission and light reflection properties when illuminated with light having wavelength(s) in the range from about four hundred (400) nanometers to about eight hundred (800) nanometers; wherein the source provides radiation having wavelength(s) in the range from about four hundred (400) nanometers to about eight hundred (800) nanometers; and wherein the detector responds to radiation having wavelength(s) in the range from about four hundred (400) nanometers to about eight hundred (800) nanometers.

6. The system of claim 4 wherein the fabric exhibits the light transmission and light reflection property when illuminated with light having wavelength(s) in the range from about four hundred (400) nanometers to about eight hundred (800) nanometers; wherein the at least one source provides radiation having wavelength(s) in the range from about four hundred (400) nanometers to about eight hundred (800) nanometers; and wherein the detector responds to radiation having wavelength(s) in the range from about four hundred (400) nanometers to about eight hundred (800) nanometers.

7. The monitoring system of claim 4, wherein the source and the detector are mounted on opposing sides of the fabric.

8. The monitoring system of claim 4, wherein the source and detector are mounted on a same side of the fabric.

9. A system for monitoring at least one predetermined physiological parameter of a wearer, comprising:

a garment, at least a portion of which garment is formed from a fabric having a first side defining an exterior surface and having a second side defining a wearer-contacting interior surface when said garment is worn by the wearer, wherein the fabric comprises a first plurality of reflective yarns knitted or woven with a second plurality of stretchable yarns, said fabric having a region thereof defining gaps of a first size between yarns when said fabric is stretched and defining gaps of a second size between yarns that is different from said first size when the fabric recovers from stretch;

at least one source of radiation having wavelength(s) in the range from about 400 to about 2200 nanometers positioned external to the fabric to direct radiation onto the exterior surface and onto the region;

at least one detector responsive to incident radiation having wavelength(s) in the range from about 400 to about 2200 nanometers, to produce a signal representative thereof, with said detector mounted to either the first side or the second side of the fabric and external to the fabric, wherein the source and detector are associated with the fabric in substantially fixed relative positions with respect to the region such that the reception of incident radiation by the detector at a first time interval when the fabric is stretched as compared to the reception of incident radiation by the detector at a second time interval when the fabric recovers from stretch is directly affected by a change in the amount of light reflected by yarns or transmitted through the gaps as the fabric of the region periodically stretches and recovers from stretch in response to at least one predetermined physiological parameter of the wearer of the garment;

a signal processor that converts periodically varying signal output received from the detector or from a data acquisition unit associated with the detector into a signal representative of the at least one predetermined physiological parameter of the wearer of the garment; and a conductive pathway disposed on or in the garment connecting the detector and the signal processor.

10. The system of claim 9, wherein the signal processor is mounted in the garment.

11. The system of claim 9, wherein the source and the detector are mounted on opposing sides of the fabric.

12. The system of claim 9, wherein the source and detector are mounted on a same side of the fabric.

* * * * *